US00PP33957P2

(12) United States Plant Patent
Masor

(10) Patent No.: US PP33,957 P2
(45) Date of Patent: Feb. 15, 2022

(54) COLEUS PLANT NAMED 'BALMAZMICK'

(50) Latin Name: *Solenostemon scutellarioides*
Varietal Denomination: Balmazmick

(71) Applicant: Ball Horticultural Company, West Chicago, IL (US)

(72) Inventor: Laura L. Masor, Grover Beach, CA (US)

(73) Assignee: Ball Horticultural Company, West Chicago, IL (US)

( * ) Notice: Subject to any disclaimer, the term of this patent is extended or adjusted under 35 U.S.C. 154(b) by 0 days.

(21) Appl. No.: 17/501,587

(22) Filed: Oct. 14, 2021

(51) Int. Cl.
*A01H 6/50* (2018.01)
*A01H 5/02* (2018.01)

(52) U.S. Cl.
USPC ..... Plt./469

(58) Field of Classification Search
USPC ..... Plt./469
See application file for complete search history.

*Primary Examiner* — Annette H Para
(74) *Attorney, Agent, or Firm* — Audrey Charles

(57) ABSTRACT

A new and distinct cultivar of *Coleus* plant named 'Balmazmick', characterized by its dark greyed purple, medium green, and cream multicolored foliage, low growth vigor, and compact-mounded growth habit, is disclosed.

1 Drawing Sheet

Latin name of genus and species of plant claimed: *Solenostemon scutellarioides.*
Variety denomination: 'Balmazmick'.

BACKGROUND OF THE INVENTION

The present invention relates to a new and distinct cultivar of *Coleus* plant botanically known as *Solenostemon scutellarioides* and hereinafter referred to by the cultivar name 'Balmazmick'.

The new cultivar originated in a controlled breeding program in Cartago, Costa Rica during May 2018. The objective of the breeding program was the development of *Coleus* cultivars with unique foliage coloration and leaf shape, compact-mounded growth habit, and good sun tolerance.

The new *Coleus* cultivar is the result of a self-pollination of the proprietary *Solenostemon scutellarioides* breeding line coded COL-1185-01, not patented, characterized by its medium pink, purple, green and white multicolored foliage, and vigorous, trailing growth habit. The new cultivar was selected as a single flowering plant within the progeny of the above stated self-pollination during March 2019 in a controlled environment in Cartago, Costa Rica.

Asexual reproduction of the new cultivar by terminal stem cuttings since March 2019 in Cartago, Costa Rica, Arroyo Grande, Calif. and West Chicago, Ill. has demonstrated that the new cultivar reproduces true-to-type with all of the characteristics, as herein described, firmly fixed and retained through successive generations of such asexual propagation.

SUMMARY OF THE INVENTION

The following characteristics of the new cultivar have been repeatedly observed and can be used to distinguish 'Balmazmick' as a new and distinct cultivar of *Coleus* plant:

1. Dark greyed purple, medium green, and cream multicolored foliage;
2. Low growth vigor; and
3. Compact-mounded growth habit.

Plants of the new cultivar differ from plants of the parent primarily in having a different foliage color, reduced growth vigor and a compact-mounded growth habit.

Of the many commercially available *Coleus* cultivars, the most similar in comparison to the new cultivar is GREAT FALLS Iguazu 'Docogrefalig', U.S. Plant Pat. No. 31,031. However, in comparison, plants of the new cultivar differ from plants of 'Docogrefalig' in at least the following characteristics:

1. Plants of the new cultivar have longer and narrower leaves than plants of 'Docogrefalig';
2. Plants of the new cultivar have an attenuate leaf base unlike the truncate base of plants of 'Docogrefalig'; and
3. Plants of the new cultivar have lower growth vigor and a more compact-mounded growth habit than plants of 'Docogrefalig'.

BRIEF DESCRIPTION OF THE PHOTOGRAPHS

The accompanying photographs show, as nearly true as it is reasonably possible to make the same in color illustrations of this type, the overall growth habit and typical foliage characteristics of the new cultivar. Colors in the photographs differ slightly from the color values cited in the detailed description, which accurately describes the colors of 'Balmazmick'. The plants were approximately 4-months old. The plants were grown in 3-gallon containers for approximately 10 weeks in an outdoor nursery in West Chicago, Ill. Plants were pinched once, four weeks prior to transplant.

DETAILED BOTANICAL DESCRIPTION

Figure 1:
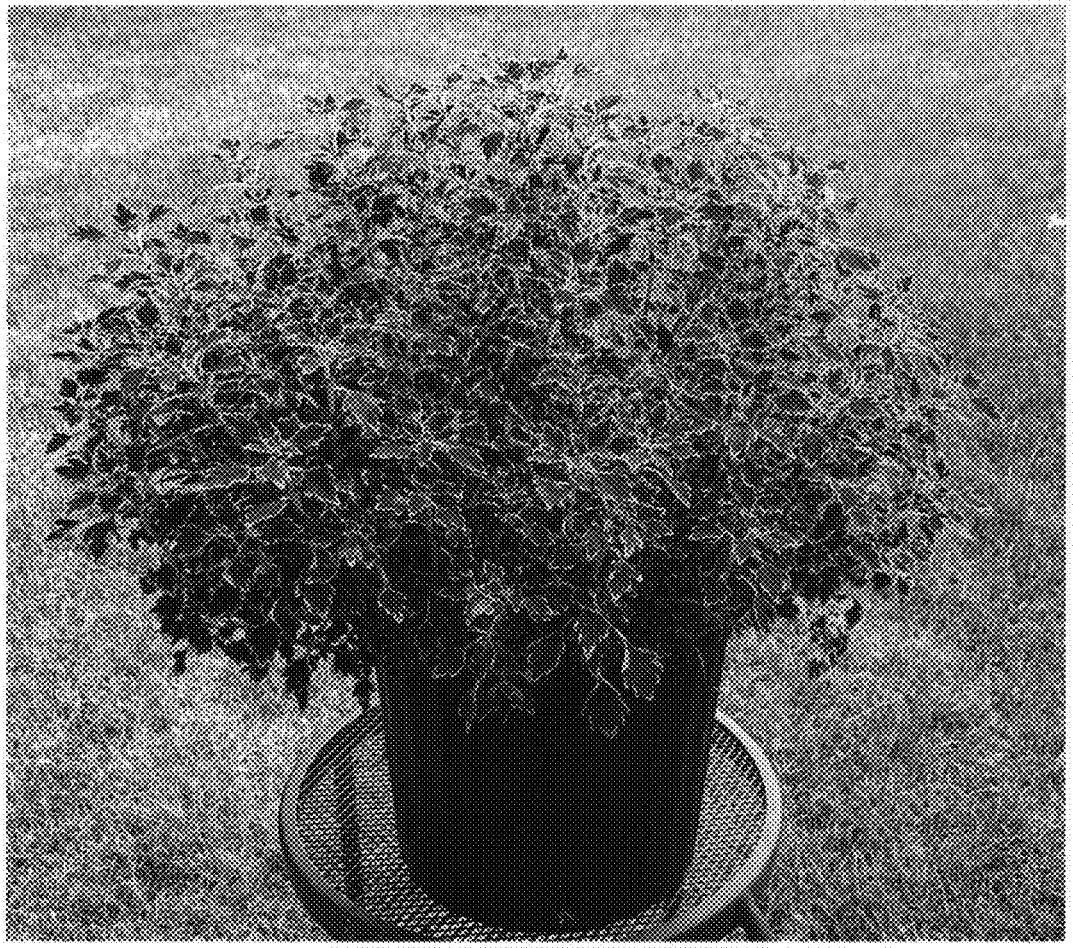
FIG. 1 illustrates a side view of the overall growth habit of 'Balmazmick'.
Figure 2:
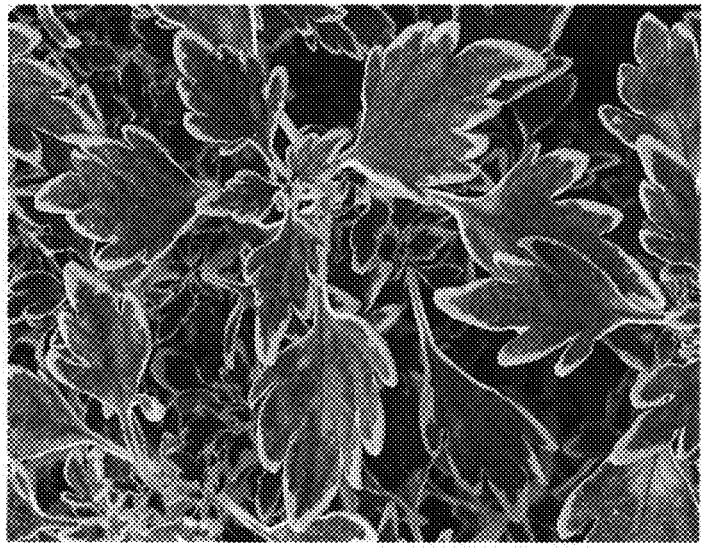
FIG. 2 illustrates a close-up view of an individual leaf of 'Balmazmick'.

The new cultivar has not been observed under all possible environmental conditions to date. Accordingly, it is possible that the phenotype may vary somewhat with variations in the environment, such as temperature, light intensity, and day length, without, however, any variance in genotype.

The chart used in the identification of colors described herein is The R.H.S. Colour Chart of The Royal Horticultural Society, London, England, 2015 edition, except where general color terms of ordinary significance are used. The color values were determined in August 2021 under natural light conditions in Naperville, Ill.

The following descriptions and measurements describe approximately 4-month-old plants produced from cuttings from stock plants and grown under conditions comparable to those used in commercial practice. The plants were grown in 3-gallon containers for approximately 10 weeks in an outdoor nursery in West Chicago, Ill. Plants were given one pinch, four weeks prior to transplant. Prior to transplant plants were grown in a polycarbonate greenhouse in West Chicago, Ill. Greenhouse temperatures were maintained at approximately 70° F. to 85° F. (21° C. to 29° C.) during the day and approximately 60° F. to 70° F. (16° C. to 21° C.) during the night. Supplemental lighting was used during propagation stage. Measurements and numerical values represent averages of typical plants.

Botanical classification: *Solenostemon scutellarioides* 'Balmazmick'.

Parentage:

*Female and male parent.*—Proprietary *Solenostemon scutellarioides* breeding line coded COL-1185-01, not patented.

Propagation:

*Type cutting.*—Terminal stem.

*Time to initiate roots.*—Approximately 4 to 6 days.

*Time to produce a rooted cutting.*—Approximately 21 to 24 days.

*Root description.*—Fibrous.

*Rooting habit.*—Freely branching.

Plant description:

*Commercial crop time.*—Approximately 6 to 8 weeks from a rooted cutting to finish in a 10 cm pot.

*Growth habit and general appearance.*—Low growth vigor, compact-mounded.

*Size.*—Height from soil level to top of plant plane: Approximately 34.0 cm. Width: Approximately 62.0 cm.

*Branching habit.*—Freely branching, pinching not required but improves basal branching. Quantity of lateral branches per plant: Approximately 12 main branches with lateral branches potentially forming at every node.

*Branch.*—Strength: Moderately strong. Shape: Square with rounded edges in cross section. Length of lateral branch: Approximately 33.0 cm. Diameter of lateral branch at central internode: Approximately 5.0 mm. Length of central internode of lateral branch: Approximately 2.5 cm. Texture: Dense minute pubescence. Color of young and mature stems: 146C.

Foliage description:

*General description.*—Quantity of leaves per lateral branch: Approximately 10. Fragrance: None. Form: Simple. Arrangement: Opposite.

*Leaves.*—Aspect: Petiole is at an acute angle to stem; leaf blade is perpendicular to stem, and transitions to an obtuse angle with age. Appearance: Matte. Shape: Elliptic. Margin: Lobed. Apex: Acute. Base: Attenuate. Venation pattern: Pinnate. Length of mature leaf: Approximately 4.0 cm. Width of mature leaf: Approximately 2.7 cm. Texture of upper surface: Sparsely pubescent. Texture of lower surface: Sparsely pubescent with densely pubescent venation. Color of upper surface of young and mature foliage: 187A with irregular mottling of 184D, margins of 144A and 155A at base; venation of 187A or indistinguishable from leaf lamina. Color of lower surface of young and mature foliage: Closest to 147C with 158D at base that is occasionally spotted with 187A; venation coloration indistinguishable from leaf lamina.

*Petiole.*—Length: Approximately 1.5 cm to 2.5 cm. Width: Approximately 2.0 mm. Texture: Densely pubescent. Color: 145C.

Flowering description: To date, flower development has not been observed on plants of the new *Coleus*.

Disease and pest resistance: To date, resistance to pathogens and pests common to *Coleus* has not been observed.

What is claimed is:

1. A new and distinct cultivar of *Coleus* plant named 'Balmazmick', substantially as herein illustrated and described.

* * * * *